United States Patent [19]
Freeman

[11] Patent Number: 5,334,137
[45] Date of Patent: Aug. 2, 1994

[54] LACRIMAL FLUID CONTROL DEVICE

[75] Inventor: Jerre M. Freeman, Memphis, Tenn.

[73] Assignee: Eagle Vision, Inc., Memphis, Tenn.

[21] Appl. No.: 839,417

[22] Filed: Feb. 21, 1992

[51] Int. Cl.⁵ .............................................. A61M 27/00
[52] U.S. Cl. .......................................... 604/8; 604/294
[58] Field of Search ................ 604/8, 9, 10, 104, 285, 604/294; 128/830, 831, 839, 842, 843, 864

[56] References Cited

U.S. PATENT DOCUMENTS

| | | | |
|---|---|---|---|
| 2,737,953 | 3/1956 | Wiltein | 604/285 |
| 3,385,300 | 5/1968 | Holter | 604/104 X |
| 3,949,750 | 4/1976 | Freeman . | |
| 4,563,182 | 1/1986 | Stoy et al. | 604/285 |
| 4,660,546 | 4/1987 | Herrick et al. . | |
| 4,747,818 | 5/1988 | Edelschick | 604/8 |
| 4,787,885 | 11/1988 | Binder | 604/8 |
| 4,915,684 | 4/1990 | MacKeen et al. | 604/8 |
| 4,959,048 | 4/1990 | Seder et al. | 604/9 |
| 5,049,142 | 6/1981 | Herrick et al. . | |
| 5,053,030 | 5/1981 | Herrick et al. . | |

*Primary Examiner*—Robert A. Hafer
*Assistant Examiner*—Sam Rimell
*Attorney, Agent, or Firm*—Bradford E. Kile; Ruffin B. Cordell

[57] ABSTRACT

There is provided a lacrimal fluid control device for blocking the flow of lacrimal fluid away from the surface of a wearer's eye through a punctal opening and into an associated caniculus. The lacrimal fluid control device includes a tip portion comprising a generally inverted truncated cone and a head portion comprising a generally enlarged dome. The tip is operable to facilitate placement of the lacrimal fluid control device at least partially through a wearer's punctal opening and the enlarged dome or head portion prevents drift of the lacrimal fluid control device completely through the punctal opening and into a generally vertical portion of an associated canaliculus.

23 Claims, 2 Drawing Sheets

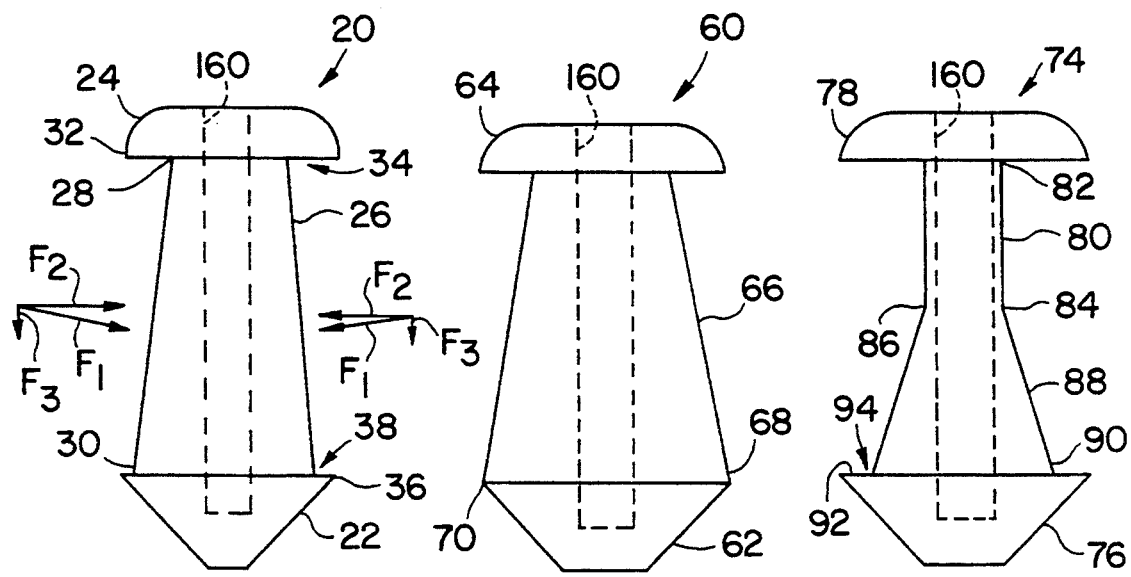
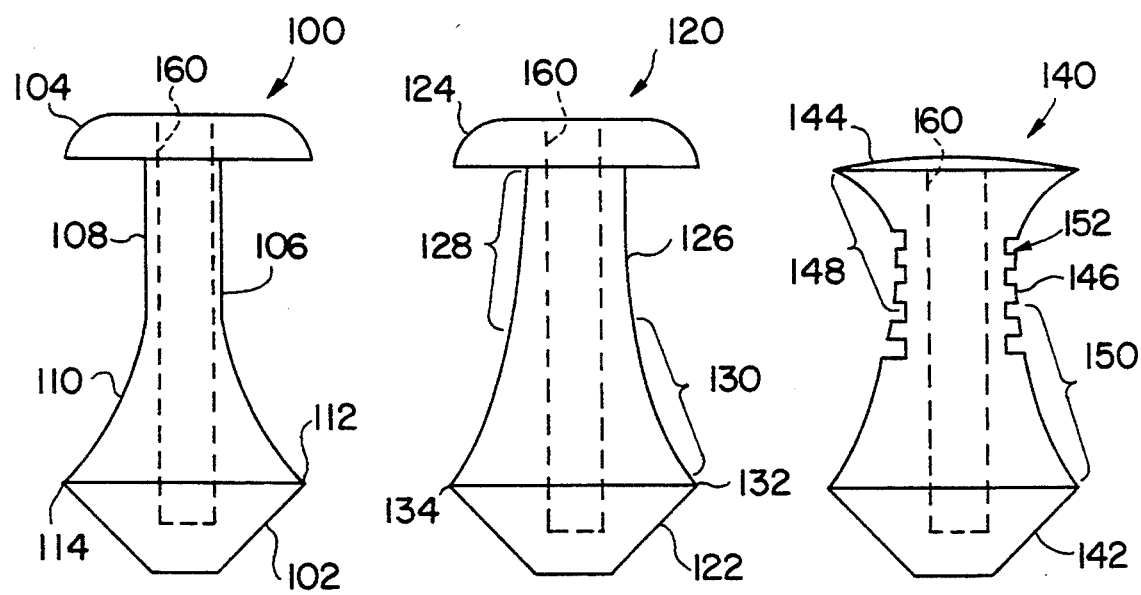

LACRIMAL FLUID CONTROL DEVICE

RELATED PATENTS

This application is related to the subject matter of prior U.S. Pat. No. 3,949,750 entitled "Puncrum Plug and Method for Treating Keratoconjunctivitis Sicca (Dry Eye) and Other Ophthalmic Aliments Using Same"; and to U.S. Pat. No. 4,915,684 entitled "Method and Apparatus For Modulating the Flow of Lacrimal Fluid Through A Puncrum and Associated Canaliculus."

BACKGROUND OF THE INVENTION

This invention relates to a device for treatment of tear-related disorders. More specifically, this invention relates an improved punctum plug for treating keratoconjunctivitis sicca and other conditions of dry eye and contact lens wearing problems as well as pathologically dilated and constricted puncta. Keratitis sicca or keratoconjunctivitis sicca or in laymen's terms "dry eye" pertain to a continuum of difficulties which range from discomfort to decreased vision and pain and in extreme circumstances blindness. The causes of dry eye are aging, disease inflammatory processes and prescription drug side effects. A common condition is an inability to maintain a stable preocular tear film (PTF).

In a healthy eye the PTF is spread over the cornea and conjunctival epithelia by the upper eyelid and makes the surface of an eye smooth and optically clear. The tear film is composed of three thin layers which coat the surface of the eye. An outermost oily layer is produced by small glands called meibomian glands which are located at the edge of the eyelid. This outermost layer provides a smooth tear surface and reduces evaporation of tears. A middle watery layer is produced by large lacrimal glands and a plurality of small glands scattered throughout the conjunctiva. This watery layer produces the largest amount of fluid and cleanses the eye by washing away foreign particles and irritants. An innermost layer consists of mucus produced by goblet cells in the conjunctiva. This inner layer allows the watery layer to spread evenly over the surface of the eye and helps the eye to remain wet. The mucus produced by this innermost layer adheres tears to the eye.

Normally the PTF is formed by a cooperative interaction of products from the memobian glands, the lacrimal glands and goblet cells. Dry eye results when those glands produce less than an adequate amount of tears or the tears are drained away or evaporate too rapidly.

Tear deficiencies cause chronic irritation of the anterior segment, resulting in complaints of sandy, itching eyes, conjunctivitis, metabolic disturbances of the cornea and extreme cases, a loss of visual function. Patients often present complaints and problems associated with a partial decrease in aqueous tear production. One cause of such complaints is partial atrophy of the lacrimal glands which is seen often in an aged patient and in some patients following infection. Atrophy can also occur in a younger patient wearing high water-contact lenses, because of the increased requirement of the anterior segment of aqueous tears.

Conditions of dry eye have been treated with various degrees of success in the past. One prior practice in treating dry eye has been to utilize various types of topical drops and ointments. Some sufferers of dry eye prefer using humidifiers and vaporizers to increase the moisture level in the surrounding air, which helps by decreasing evaporation of lacrimal fluid from the eye.

More recently, permanent punctal occlusion has proven to be an effective method of treating tear-related disorders including dry eye, corneal ulcers, conjunctivitis, blepharitis, contact lens problems and other external eye diseases. In extreme cases of discomfort and pain, such as occur in Sjogren's syndrome, permanent closure of the puncta and canaliculi by surgery or cauterization has produced at least some success. Thermal occlusion was initially performed with cautery or diatherapy, and is now more frequently performed with the aid of medical grade lasers. When PTF loss into the naso-lacrimal trap is blocked, the volume of the remaining tears provide enhanced wetness of the anterior segment.

Each of the aforementioned treatments, however, possess certain inherent limitations. Topical drops and ointments require frequent re-applications. Humidifiers and vaporizers are relatively bulky and must be connected to an electrical source and, thus, are not satisfactory for all occasions, such as outdoor activities. Finally, surgical or cauterization procedures are costly and create a danger of subsequent epiphora and/or infection, the destruction of normal tissue requires surgical intervention to reverse.

In order to avoid one or more of the foregoing disadvantages, alternative methods of temporary or reversible occlusion of a punctal opening have been envisioned. Such methods include temporary occlusion of the canaliculus by the insertion of small rods made from gelatin or collagen, or the use of temporary plugs made from bone cement. The blocking action of these agents is either to brief or otherwise unsatisfactory.

The foregoing noted problems of mild to moderate dry eye were advantageously addressed by the introduction of a punctum plug which advantageously provides reversible punctal occlusion as disclosed and claimed in the previously identified Freeman U.S. Pat. No. 3,949,750. The disclosure of this patent, of common inventorship with the subject invention, is incorporated here in by reference as though set forth at length.

Occlusion of a lower and/or upper punctum with medical grade silicone plugs of the Freeman design has proven to be highly beneficial in a number of patients suffering from dry eye conditions.

It has been found however, that in certain instances a punctum plug of previously known designs have been subject to occasional extrusion or accidental removal by a patient rubbing the corner of an eye. Accordingly, it would be highly desirable to facilitate the retention and function integrity of a punctum plug within the punctum of a patient's eye while providing the advantages of reversibly blocking the flow of lacrimal fluid from the eye.

The problem suggested in the proceeding are not intended to be exhaustive, but rather are among many which may tend to reduce the effectiveness of prior methods and apparatus for blocking the flow of lacrimal fluid through a punctum and associated canaliculus. Other noteworthy problems may also exist; however, those presented above should be sufficient to demonstrate that devices for treating the loss of PTF appearing in the past will admit to worthwhile improvement.

OBJECTS AND SUMMARY OF THE INVENTION

Objects

It is therefor a general object of the invention to provide a novel and improved lacrimal fluid control device which will block the drainage of lacrimal fluid through the puncta and canaliculus of a wearer.

It is another object of the invention to provide a novel apparatus to alleviate symptoms of PTF loss without surgically occluding the puncta of a patient's eye.

It is yet another object of the invention to enhance the retention of PTF for patients having pathologically dilated or constricted puncta with a device which may be facilely inserted and reversibly removed.

It is still another object of the invention to provide a novel lacrimal fluid control device operable to minimize incidental and undesired extrusion of the device from a patient's punctal opening.

It is a further object of the invention to provide a novel lacrimal fluid control device which will be operable to advantageously utilize the psychology of a wearer's punctal opening to enhance retention of the device.

It is yet a further object of the invention to provide a lacrimal fluid control device wherein a snug retention of the device with a head portion tucked into a shallow depression around a wearer's punctal opening is insured.

BRIEF SUMMARY OF THE INVENTION

One preferred embodiment of the invention which is intended to accomplish at least some of the foregoing objects comprises a lacrimal fluid control device for blocking the flow of lacrimal fluid away from the surface of a wearer's eye through a punctal opening and into an associated caniculus.

The lacrimal fluid control device includes a tip portion comprising a generally inverted truncated cone and a head portion comprising a generally enlarged dome. The tip is operable to facilitate placement of the lacrimal fluid control device at least partially through a wearer's punctal opening and the enlarged dome or head portion prevents drift of the lacrimal fluid control device completely through the punctal opening and into a generally vertical portion of an associated canaliculus.

A shank portion is integrally joined between the tip portion and the head portion, and is operably engaged about its periphery by a punctal opening ring fibroelastic of tissue of a patient. The shank portion has a diameter adjacent to the head portion which is less in diameter than the diameter of the shank portion adjacent the tip. With this dimensional relationship, lateral forces of the surrounding fibroelastic tissue of the punctal opening against the shank portion produces a resultant force vector on the shank portion which is directed toward the tip of the lacrimal fluid control device. This resulting force facilitates retention of the lacrimal fluid control device within the punctal opening with the head portion sealed within a shallow depression leading into the punctal opening.

In a most preferred embodiment of the invention, the shank portion includes at a cylindrical segment which is integrally joined to the head portion of the lacrimal fluid control device and a truncated conical portion which is integrally joined with the tip portion of the lacrimal fluid control device. In other preferred embodiments of the invention, the shank portion is arcuate from the head portion to the tip. In still a further preferred embodiment a plurality of annular depression or projection retaining rings are fashioned into the surface of the shank portion.

THE DRAWINGS

Other objects advantages of the present invention will become apparent from the following detailed description of preferred embodiments taken in conjunction with the accompanying drawings wherein:

FIG. 1 is a pictorial view disclosing the anatomy of a human eye including a lower punctal opening that opens into a canaliculus which is connected to a lacrimal sack and ultimately the nasal passage of a human.

FIG. 2 is a detail side view, in partial section, of a circular area identified in FIG. 1 which depicts a lacrimal fluid control device of the subject invention in a posture blocking PTF flow into a patient's canaliculus wherein a tip portion extends through a punctal ring and a head portion is seated within a generally conical depression adjacent the patient's punctal opening. A shank portion having outwardly flared sidewall surfaces is positioned through the punctal opening and receives forces of the punctal ring tissue which operably retains the punctum plug in position.

FIG. 3, note sheet two, is a side view of one embodiment of the subject lacrimal fluid control device including a shank portion having outwardly sloping sidewall surfaces.

FIG. 4, note again sheet one, is a plan view of a lacrimal fluid control device as depicted in FIG. 3.

FIG. 5 is a side elevation view of a variation of the lacrimal fluid control device depicted in FIG. 3.

FIG. 6 is a side view of a most preferred embodiment of the subject lacrimal fluid control device including a shank portion having a cylindrical segment and a integrally fashioned truncated cone.

FIG. 7 is a variation of a lacrimal fluid control device as depicted in FIG. 6 wherein the truncated conical segment is produced with outwardly arcuate or concave sidewall surfaces.

FIG. 8 is a further embodiment of the subject lacrimal control device wherein the outward sidewall surface of the shank portion is arcuate from the head to the tip and the radius of curvature adjacent the head portion is greater than the radius of curvature adjacent the tip portion of the control device.

FIG. 9 is yet a further embodiment of the subject lacrimal fluid control device wherein the sidewall surface of the shank portion is arcuate and the radius of curvature adjacent the tip portion is greater than the radius of curvature adjacent the head portion of the control device.

DETAILED DESCRIPTION

Context of the Invention

Figure 1:
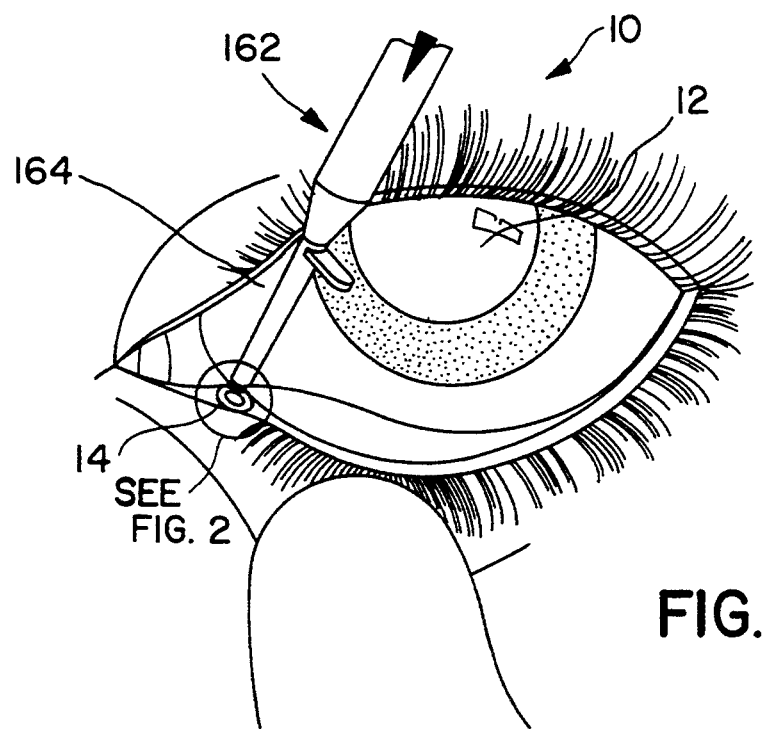

Before discussing in detail a new and useful non-biodegradable, lacrimal fluid, control device for blocking the flow of lacrimal fluid from the surface of an eye through a punctal opening and into an associated canaliculus, it may be useful to briefly discuss the context of the invention in association with FIG. 1. More specifically, the anatomy of an eye 10 is illustrated including an outer corneal surface 12 which is lubricated by a thin PTF coating the surface of the eye. As noted above, this thin film is composed of three layers: an outer oily layer, an intermediate watery layer and an innermost layer of mucous.

The PTF or lacrimal fluid is produced by glands at the edge of the eyelid such as meibomian glands, small glands scattered throughout the conjunctiva and by a major tear gland called the large lacrimal gland. As a human blinks, the PTF is distributed over the surface of the eye and is optically clear. Without adequate PTF, good vision would not be possible and a patient may encounter symptoms of stinging, burning, scratchiness, stringy mucus and excess irritation from smoke.

Tears which lubricate the eye are produced continuously with excessive PTF being drained away from the eye surface through an upper (not shown) and lower punctal opening 14. Once the PTF passes through the punctal opening progression continues into a canal or duct known as the canaliculus. From the canaliculus, the excess lacrimal fluid drains into a lacrimal sack and ultimately into the nasal cavity.

The punctum is the proximal opening 14 of the canaliculus which leads from the inner or medial lid margin to the lacrimal or tear sack. There are normally two punctum openings for each eye, one in the upper medial lid and one in the lower medial portion of the lid. It is an opening which is usually round, oval or sometimes slit-like in shape and varies in size but is usually somewhere under one millimeter in diameter in a normal human adult. The punctum opening 14 is announced by a slightly larger opening, which is somewhat like a funnel and which comes down and gets smaller as it plunges interiorly in the lower lid and superiorly in the upper lid before a larger portion of the canaliculus is encountered called the ampulla. The vertical portion of the canaliculus then turns and runs generally horizontally toward the lacrimal sack.

The proximal end of the canaliculus, as discussed above, is often referred to as the punctal ring. Although the punctum and its associated anatomy acts somewhat like a sphincter or with a true sphincter muscle surrounding it, this tissue is best described as elastic, collagen-type material which is in the shape of a sphincter or punctal ring. When the punctum is dilated, this fibroelastic material distends. When the dilation is finished, it has enough memory to constrict again, bringing the punctal neck or opening down to its previous size unless it has been over distended or some of the elastic fibers are broken. In sum, the punctal openings act somewhat like a sphincter muscle and produce forces that enhance the canalicular proximal opening and the punctum as if it were an active muscle. The forces which are engendered here are constricted into this area into a generally horizontal direction.

Lacrimal Fluid Control Device

It is a primary purpose of the subject invention to advantageously utilize the elastic tissue forces of the punctal ring to conform and cooperate with a lacrimal fluid control device to maintain the device in an advantageous position for reversibly blocking the flow of PTF from the surface of a wearer's eye.

Figure 2:
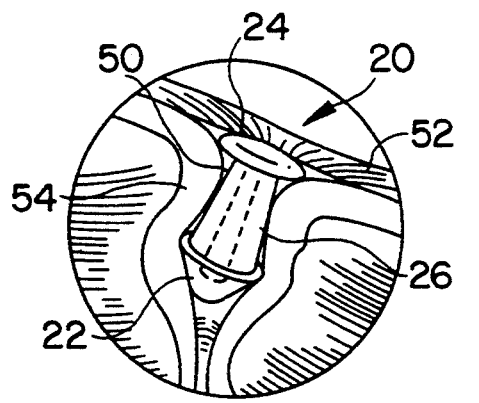
Figure 4:
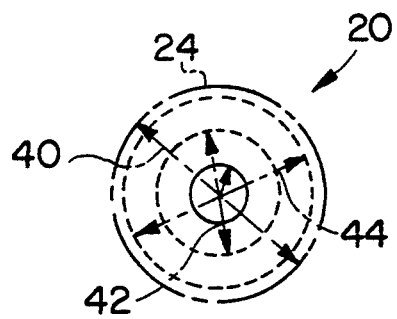

Turning now to the drawings and in particular to FIGS. 2–4, there will be seen one preferred embodiment of the subject invention wherein a lacrimal fluid control device 20 is depicted having a tip portion 22 composed of a generally inverted truncated cone and a head portion 24 comprising a generally enlarged dome. A shank portion or segment 26 interconnects the tip 22 with the head 24. The shank portion 26 is configured, in the embodiment illustrated in FIGS. 2–4 in the shape of a generally elongate truncated cone having a small diameter end 28 connected to the head portion 24 and a larger diameter end 30 connected to a base portion of the tip 22. The diameter of the small end 28 of the truncated cone has a value less than the diameter 32 of the adjacent head 24 and thus a lip region 34 is fashioned at the base of the head. In a similar manner, the diameter of tip 22 at its base 36 is greater than the diameter of the shank portion at its base 30. Thus a peripheral lip is fashioned at the interface between the shank 26 and tip 27 as illustrated in FIG. 3.

The circular symmetric character of the lacrimal fluid control device 20, as discussed in connection with FIG. 3, is illustrated in the top view depicted in FIG. 4, note again sheet 1. In this view, the outer diameter 40 of the head 24 is seen to be considerably larger than the diameter of the diameter 42 the small end 28 of the truncated cone 26 comprising the shank. In a similar manner, the diameter 44 of the base 30 of the truncated cone 36 forming the shank is shown to be less than the diameter 40 of the base of the tip 22 such that in each instance, and as previously noted, there is a peripheral lip 34 and 38 fashioned about the head and tip respectively as it joins with the interconnecting shank 26.

Turning now specifically to FIG. 2, as illustrated on sheet 1, the subject lacrimal fluid control device 20 is shown positioned through a punctal opening 50. In this, it will be noted that the head 24 of the lacrimal fluid control device 20 fits into a funnel shaped recess 52 adjacent the punctal opening 50. The tip 22 of the lacrimal fluid control device has been inserted through the punctal opening 50 and is positioned in the generally vertical portion of the associated canaliculus.

The fibroelastic punctal ring tissue 54 is self constricting about the shank portion 26 of the lacrimal fluid control device 20 and advantageously cooperates with the peripheral ledge 38 adjacent the tip to secure the control device in a preferred operative position. In this connection, attention is invited again to FIG. 3, note sheet 2 of the drawings, wherein forces F1 of a vector diagram represent the normal force of the fibrioelastic material imparted to the side surfaces of the shank 26. Normal forces F1 may be resolved in two vector components F2 directed generally horizontally of equal and opposite magnitude about the shank 26 and downwardly directed vectors F3 as depicted in FIG. 3. The downward vectors F3 do not self cancel and thus a net resultant force is imparted downward on the lacrimal fluid control device from the surrounding tissue by virtue of the fact of the outwardly sloping exterior walls of the shank portion 26. Accordingly, as depicted in FIG. 2, the fibroelastic material facilitates retention of the lacrimal fluid control device 20 in an advantageously operative position with the head 24 position in the shallow funnel recess 52 and snugly adjacent the punctal opening 50.

Turning now to FIG. 5 there will be seen another embodiment of the subject invention wherein a lacrimal fluid control device 60 is depicted with a tip portion 62, a head portion 64 and an interconnecting shank 66. The tip 62 and head portion 64 are substantially identical with tip portion 22 and head portion 64 of the embodiment of the invention depicted in FIG. 3. It will be seen however, that the exterior configuration of the interconnecting shank portion 66 is in the general shape again of a truncated cone where the large diameter of the truncated cone comprising the shank portion 66 at 68 is identical to the diameter 70 of the base of the truncated cone comprising the tip portion 62.

In the embodiment discussed in connection with FIG. 5, there is no peripheral lip fashioned about the junction zone between the shank and tip such as zone 38 depicted in the embodiment illustrated by FIG. 3. Notwithstanding, the lack of a anchoring zone 38 the lacrimal control device 60, as illustrated in FIG. 5, is securely retained in an operating posture within a punctal opening by downwardly directed force vectors formed by the fibroelastic punctal ring material as discussed in connection with FIG. 3.

Turning now to FIG. 6, there will be depicted a further embodiment of the subject invention. In this, a lacrimal fluid control device 74 is shown having a tip portion 76 and a head portion 78 substantially identical with the tip 22 and head portion 24 of the embodiment depicted in FIG. 3. The interconnecting shank portion of the embodiment shown in FIG. 6, however, is considerably different and includes a cylindrical segment 80 which is connected at one end 82 to the base of the head portion 78. The other end 84 of the cylindrical segment 80 is joined onto a small end 86 of a truncated cone 88 comprising a second segment of the shank portion. A base 90 of the truncated cone 88 is joined with a base 92 of the tip 76. In the embodiment depicted in FIG. 6, the diameter of the base at 90 is less than the diameter of the base at 92 and thus a peripheral retaining ring or lip 94 is fashioned about the junction of the shank with the tip. The embodiment of the subject invention depicted in FIG. 6 is the best mode contemplated by the inventor of practicing the invention at the time of filing of the application for patent.

Turning now to FIG. 7, there will be seen yet another embodiment of the subject invention wherein a lacrimal fluid control device 100 is shown having a tip portion 102 and a head portion 104. The tip is interconnected to the head through an interconnecting shank 106. The shank 106 has a cylindrical upper portion 108 and a lower portion in the general configuration of a truncated cone 110. In this, the embodiment of FIG. 7 is similar to that of FIG. 6. The exterior configuration, however, of the sidewalls of the truncated cone 110 are different in that they are arcuate and concave outwardly. Moreover, the diameter of the base 112 of the cone 110 is equal to the diameter of the base 114 of the truncated cone forming the tip 102.

Referring now to FIG. 8, there is yet another embodiment of the subject lacrimal fluid control device invention. In this embodiment, a control device 120 includes a tip portion 122 and head portion 124 which are substantially identical with the tip 22 and head portion 24 of the embodiment depicted in FIG. 3 and subsequent embodiments illustrated in FIGS. 5, 6 and 7. The shank portion 126 of the embodiment illustrated in FIG. 8, however, is different in configuration and includes an arcuate curvature of the sidewalls. An upper segment 128 of the shank portion 126 is configured with a longitudinal sidewall curvature having a radius of curvature which is relatively long and thus the upper segment is substantially cylindrical in configuration. A lower segment 130 of the shank portion, has a shorter radius of curvature as compared with the upper segment and terminates with a base portion 132 having a diameter identical with the diameter of a base portion 134 of the tip 132.

FIG. 9 is still another specific embodiment of the subject invention wherein a lacrimal fluid control device 140 is illustrated with a tip portion 142 and head portion 144. The tip portion 142 is interconnected with the head through an intervening shank portion 146. The shape of the tip 142 is substantially identical with the shape of the tip in all prior embodiments of the invention and comprises a generally inverted truncated cone which is operable to facilitate insertion of the lacrimal fluid control device through a wearer's punctal opening.

The head portion of the embodiment depicted in FIG. 9 is by comparison with the head portions of prior embodiments rather shallow in nature and comprising an arcuate dome. The shank portion 146 which interconnects the head 144 and tip 142 is composed of two principal segments. An upper segment 148 is an inverted truncated cone with an arcuate sidewall configuration and a lower segment 150 of the interconnecting shank portion 146 is also composed of a generally truncated cone with arcuate sidewalls. The radius of curvature of the upper segment 148 is less than the radius of curvature of the lower segment 150 as illustrated in FIG. 9.

The sidewalls of the shank portion 146 are further fashioned with a plurality of peripheral rings 152 which in a preferred embodiment are fashioned in a series of four annular recesses in sequence. Alternatively the annular recesses may be projections about the shank.

The previously noted lacrimal fluid control devices may be formed from a plurality of biologically inert materials such as polytetrafluorethylene (Teflon), hydroxyethylmethacrylate (HEFLA), polymethylmethacrylate, (PMFLA) and various compositions of medical grade silicon, etc.

Method of Insertion

With each of the specific embodiments discussed above, an axial bore 160 is fashioned from the head to the tip and operably receives a similarly dimensioned tip of an insertion tool 162, note FIG. 1 on sheet 1. The insertion tool enables a physician to pick up a lacrimal fluid control device and carry it on the tip of the insertion tool 162 and then utilizing the tool and a displacement sleeve 164 operably deposit the lacrimal fluid control device through the punctal opening and into an operative position such as depicted in FIG. 2. This procedure is described in greater detail in the above referenced U.S. Pat. No. 4,915,684. The disclosure of this document is incorporated by reference as though set forth at length.

BRIEF SUMMARY OF MAJOR ADVANTAGES OF THE INVENTION

In describing various embodiments of a lacrimal fluid control device, for efficiently and reversibly blocking the flow of lacrimal fluid from the surface of an eye through a punctal opening and associated canaliculus, those skilled in the art will recognize several advantages which singularly distinguish the subject invention from the heretofore known prior art.

A particular advantage of the subject invention, is the provision of the shank portion, intermediate a tip and head portion of a lacrimal fluid control device wherein the diameter of the shank adjacent the head is less than the diameter of the shank adjacent the tip and interconnecting sidewalls are sloped outwardly from the head to the tip of the control device. This outwardly sloped sidewall provides an opportunity for fibroelastic tissue surrounding the punctal opening to impart a resulting downward force on the lacrimal fluid control device to operably retain the punctum plug in a secure operative position such as depicted in FIG. 2.

In a best mode, the shank 80 is cylindrical adjacent the head and conical in a lower segment to advantageously conform to the natural configuration of the punctal opening. In other embodiments, the conical sidewall surfaces are arcuate and in one embodiment the radius of curvature is greatest adjacent the head portion and in another embodiment having a reduced height head the radius the curvature adjacent the head is less than that the adjacent the tip of the control device.

In each of the various embodiments depicted in FIGS. 3-9, peripheral retaining rings may be fashioned to further enhance the retention the lacrimal fluid control device in an operative posture which will minimize inadvertent removal by a wearer.

In describing the invention, reference has been made to preferred embodiments. Those skilled in the art, and familiar with the disclosure of the subject invention, may recognize additions, deletions, modifications, substitutions and/or other changes which will fall within the purview of the invention as designed in the following claims.

What is claimed is:

1. A lacrimal fluid control device for blocking the flow of lacrimal fluid from the surface of an eye through a punctal opening and into an associated canaliculus, said lacrimal fluid control device comprising:

a tip portion comprising a generally inverted truncated cone and being operable to facilitate placement of the lacrimal fluid control device at least partially through a punctal opening of a wearer and into a generally vertical portion of an associated canaliculus;

a head portion;

a shank portion integrally joined at one end to said head portion and at the other end to said tip portion, said head portion comprising a generally enlarged dome with respect to said shank portion at said one end and being integrally joined to said head portion and operable to prevent drift of the lacrimal fluid control device completely through the punctal opening and into the generally vertical portion of the associated canaliculus, said shank portion interconnecting said head and tip portions and being operably engaged about its periphery by a punctal opening ring of tissue of a patient, said shank portion having, a diameter at the junction of said shank portion with said head portion which is less than the diameter of said shank portion at the junction of said shank portion with said tip portion such that;

said shank portion having at least one segment that slopes outwardly along a longitudinal position of said shank from a position relatively closer to said head portion than said tip portion to a position relatively closer to said tip portion than said head portion, lateral closing force of the punctal opening ring of tissue against said shank portion produces a resultant force vector on the shank portion which is directed toward the tip of the lacrimal fluid control device to facilitate retention of the lacrimal fluid control device within the punctal opening to block the flow of lacrimal fluid from the surface of an eye through the punctal opening and into an associated canaliculus.

2. A lacrimal fluid control device for blocking the flow of lacrimal fluid from the surface of an eye through a punctal opening as defined in claim 1 wherein:

said shank portion is configured in the shape of a truncated cone with a small diameter end of the truncated cone joined to said head portion of said lacrimal fluid control device and a large diameter end of the truncated cone joined to a base of the truncated cone comprising said tip portion of said lacrimal fluid control device.

3. A lacrimal fluid control device for blocking the flow of lacrimal fluid from the surface of an eye through a punctal opening as defined in claim 2 wherein:

the small diameter end of said truncated cone of said shank portion is less in diameter than the diameter of the associated segment of said head portion.

4. A lacrimal fluid control device for blocking the flow of lacrimal fluid from the surface of an eye through a punctal opening as defined in claim 2 wherein:

the large diameter end of said truncated cone of said shank portion has a diameter less than the diameter of the associated segment of the base of the truncated cone comprising said tip portion of said lacrimal fluid control device.

5. A lacrimal fluid control device for blocking the flow of lacrimal fluid from the surface of an eye through a punctal opening as defined in claim 2 wherein:

the large diameter end of said truncated cone of said shank portion has a diameter equal the diameter of the associated segment of the base of the truncated cone comprising said tip portion of said lacrimal fluid control device.

6. A lacrimal fluid control device for blocking the flow of lacrimal fluid from the surface of an eye through a punctal opening as defined in claim 1 wherein:

side surfaces of said shank portion of said lacrimal fluid control device being arcuate throughout the length of said shank portion from the base to the tip portion of the lacrimal fluid control device.

7. A lacrimal fluid control device for blocking the flow of lacrimal fluid from the surface of an eye through a punctal opening as defined in claim 6 wherein:

the radius of curvature of said arcuate side surfaces of said shank portion is greater at the location of the shank portion adjacent to said head portion of said lacrimal fluid control device than the radius of curvature of said arcuate side surfaces of said shank portion adjacent said tip portion of said lacrimal fluid control device.

8. A lacrimal fluid control device for blocking the flow of lacrimal fluid from the surface of an eye through a punctal opening as defined in claim 7 wherein:

the diameter at a base of said shank portion equals the diameter of a base of the truncated cone comprising said tip portion of said lacrimal fluid control device.

9. A lacrimal fluid control device for blocking the flow of lacrimal fluid from the surface of an eye through a punctal opening as defined in claim 7 wherein:

the diameter at a base of said shank portion is less than the diameter of a base of the truncated cone comprising said tip portion of said lacrimal fluid control device.

10. A lacrimal fluid control device for blocking the flow of lacrimal fluid from the surface of an eye through a punctal opening as defined in claim 6 wherein:

the radius of curvature of said arcuate side surfaces of said shank portion adjacent said tip portion is greater than the radius of curvature of the arcuate side surfaces of said shank portion adjacent said head portion of said lacrimal fluid control device.

11. A lacrimal fluid control device for blocking the flow of lacrimal fluid from the surface of an eye through a punctal opening as defined in claim 10 wherein:
the diameter of said shank portion having arcuate side surfaces at the base of said shank portion equals the diameter of a base of said truncated cone comprising said tip portion of said lacrimal fluid control device.

12. A lacrimal fluid control device for blocking the flow of lacrimal fluid from the surface of an eye through a punctal opening as defined in claim 11 wherein:
at least one peripheral recess is fashioned about said arcuate shank portion of said lacrimal fluid control device to facilitate retaining engagement of said lacrimal fluid control device with surrounding punctal tissue.

13. A lacrimal fluid control device for blocking the flow of lacrimal fluid from the surface of an eye through a punctal opening as defined in claim 12 wherein:
said at least one peripheral recess comprises a plurality of four annular recesses about said arcuate shank portion of said lacrimal fluid control device.

14. A lacrimal fluid control device for blocking the flow of lacrimal fluid from the surface of an eye through a punctal opening and into an associated canaliculus, said lacrimal fluid control device comprising:
a tip comprising a generally inverted truncated cone and being operable to facilitate placement of the lacrimal fluid control device at least partially through a punctal opening of a wearer and into a generally vertical portion of an associated canaliculus;
a head portion operable to prevent drift of the lacrimal fluid control device completely through the punctal opening and into the generally vertical portion of the associated canaliculus;
a shank integrally joined at one end to said head and at the other end to said tip, said shank interconnecting said head and tip and being operably engaged about its periphery by a punctal opening ring of tissue of a patient, said shank having,
a generally cylindrical segment with a diameter at said one end adjacent to said head which is less than the diameter of said head, and
a truncated conical segment with a small diameter and joined to said cylindrical segment and a large diameter end at said other end of said shank such that;
lateral force of the ring of tissue of the punctal opening against said shank produces a resultant force vector on the shank which is directed toward the tip of the lacrimal fluid control device to facilitate retention of the lacrimal fluid control device within the punctal opening with the head against the punctal ring tissue.

15. A lacrimal fluid control device for blocking the flow of lacrimal fluid from the surface of an eye through a punctal opening as defined in claim 14 wherein:
the diameter of said other end of said shank is less than the diameter of the base of the truncated cone comprising said tip of said lacrimal fluid control device.

16. A lacrimal fluid control device for blocking the flow of lacrimal fluid from the surface of an eye through a punctal opening as defined in claim 14 wherein:
the diameter of said other end of said shank is equal to the diameter of the base of the truncated cone comprising said tip of said control device.

17. A lacrimal fluid control device for blocking the flow of lacrimal fluid from the surface of an eye through a punctal opening as defined in claim 14 wherein:
the side surfaces of said truncated generally conical segment are arcuate and concave from the generally cylindrical segment to the tip of the lacrimal fluid control device.

18. A lacrimal fluid control device for blocking the flow of lacrimal fluid from the surface of an eye through a punctal opening as defined in claim 17 wherein:
at least one peripheral recess is fashioned about said shank portion of said lacrimal fluid control device to facilitate retaining engagement of said lacrimal fluid control device with surrounding punctal tissue.

19. A lacrimal fluid control device for blocking the flow of lacrimal fluid from the surface of an eye through a punctal opening and into an associated canaliculus, said lacrimal fluid control device comprising:
a tip portion comprising a generally inverted truncated cone and being operable to facilitate placement of the lacrimal fluid control device at lest partially through a punctal opening of a wearer and into a generally vertical portion of an associated canaliculus;
a head portion being operable to prevent drift of the lacrimal fluid control device completely through the punctal opening and into the generally vertical portion of the associated canaliculus;
a shank portion integrally joined at one end to said head portion and at the other end to said tip portion, said shank portion interconnecting said head and tip portions and being operably engaged about its periphery by a punctal opening ring of tissue of a patient, said shank portion,
being configured with a first segment in the shape of a cylinder connected at one end to the associated head portion and with a second segment in the shape of a generally truncated cone having a small diameter end connected to the other end of said cylinder and a large diameter end connected to a base portion of the truncated cone comprising said portion of said lacrimal fluid control device, and
having a diameter adjacent to said head portion which is less than the diameter of said shank portion adjacent to said tip portion such that;
lateral closing force of the punctal opening ring of tissue against said shank portion produces a resultant force vector on the shank portion which is directed toward the tip of the lacrimal fluid control device to facilitate retention of the lacrimal fluid control device to within the punctal opening to block the flow of lacrimal fluid from the surface of an eye through the punctal opening and into an associated canaliculus.

20. A lacrimal fluid control device for blocking the flow of lacrimal fluid from the surface of an eye through a punctal opening as defined in claim 19 wherein:
side surfaces of said generally truncated conical segment of said shank portion being arcuate and concave for receiving intimate contract with the punctal ring of tissue of the eye of a wearer.

21. A lacrimal fluid control device for blocking the flow of lacrimal fluid from the surface of an eye through a punctal opening as defined in claim 19 wherein:

side surfaces of said generally truncated conical segment of said shank portion being substantially linear for receiving intimate contact with the punctal ring of tissue of the eye of a wearer.

22. A lacrimal fluid control device for blocking the flow of lacrimal fluid from the surface of an eye through a punctal opening as defined in claim 20 or 21 wherein: the diameter of the base portion of the truncated conical segment of said shank portion is less than the diameter of the base of the truncated cone comprising said tip portion of said lacrimal fluid control device.

23. A lacrimal fluid control device for blocking the flow of lacrimal fluid from the surface of an eye through a punctal opening as defined in claim 20 or 21 wherein: the diameter of the base portion of the truncated conical segment of said shank portion is equal to the diameter of the base of the truncated cone comprising said tip portion of said control device.

* * * * *